US012577616B2

(12) United States Patent
Campbell

(10) Patent No.: US 12,577,616 B2
(45) Date of Patent: Mar. 17, 2026

(54) MULTIPLEX METHOD OF PREPARING A SEQUENCING LIBRARY

(71) Applicant: IDENTIGEN LIMITED, Dublin (IE)

(72) Inventor: Nathan Campbell, Twin Falls, ID (US)

(73) Assignee: IDENTIGEN LIMITED, Dublin (IE)

( * ) Notice: Subject to any disclaimer, the term of this patent is extended or adjusted under 35 U.S.C. 154(b) by 955 days.

(21) Appl. No.: 17/640,905

(22) PCT Filed: Sep. 11, 2020

(86) PCT No.: PCT/EP2020/075529
§ 371 (c)(1),
(2) Date: Mar. 7, 2022

(87) PCT Pub. No.: WO2021/048393
PCT Pub. Date: Mar. 18, 2021

(65) Prior Publication Data
US 2022/0411861 A1     Dec. 29, 2022

Related U.S. Application Data

(60) Provisional application No. 62/898,752, filed on Sep. 11, 2019.

(30) Foreign Application Priority Data

Sep. 19, 2019     (EP) ..................................... 19198454

(51) Int. Cl.
*C12Q 1/6869*     (2018.01)
*C12N 15/10*     (2006.01)
*C12Q 1/6806*     (2018.01)
*C12Q 1/6844*     (2018.01)

(52) U.S. Cl.
CPC ....... *C12Q 1/6869* (2013.01); *C12N 15/1065* (2013.01); *C12Q 1/6806* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

2016/0304948 A1 * 10/2016 Lee ...................... C12Q 1/6855
2017/0226582 A1    8/2017 Xie
2018/0334712 A1   11/2018 Singer et al.

FOREIGN PATENT DOCUMENTS

| GB | 2536446 B | 6/2020 | |
| WO | 2015126766 A1 | 8/2015 | |
| WO | 2017044100 A1 | 3/2017 | |
| WO | 2018237092 A1 | 12/2018 | |
| WO | WO-2020131383 A1 * | 6/2020 | ........... C12Q 1/6869 |

OTHER PUBLICATIONS

A novel multiplex analysis of filaggrin polymorphisms: A universally applicable method for genotyping, Clinica Chimica Acta, 413, 1488-1492 (Year: 2012).*
Targeted Amplicon Sequencing (TAS): A Scalable Next-Gen Approach to Multilocus, Multitaxa Phylogenetics, Genome Biology and Evolution, 3, 1312-1323 (Year: 2011).*
A novel multiplex analysis of filaggrin polymorphisms: A universally applicable method for genotyping, 413, 19-20, 1488-1492 (Year: 2012).*
Bybee, Seth M. et al., Targeted Amplicon Sequencing (TAS): A Scalable Next-Gen Approach to Multi locus, Multitaxa Phylogenetics, Genome Biology and Evolution, 2011, 1312-1323, 3.
Meldgaard, Michael et al., A novel multiplex analysis of filaggrin polymorphisms: A universally applicable method for genotyping, Clinica Chimica Acta, 2012, 1488-1492, 413(19).
Hammet, Fleur et al., Hi-Plex2: a simple and robust approach to targeted sequencing-based genetic screening, BioTechniques, 67, 118-122, 2019.
Illumina, Illumina Adapter Sequences, illumina, N/A, 1-53, 2020.
Iontorrent, Ion AmpliSeq Custom DNA Panels, ThermoFisher Scientific, N/A, 1-2, 2016.
Massir, et al., Targeted DNA Methylation Analysis by Next-generation Sequencing, Journal of Visualized Experiments, 96, pp. 1-11, Feb. 2015.
Nguyen-Dumont, Tú et al., A high-plex PCR approach for massively parallel sequencing, BioTechniques, 55:2, 69-74, 2013.
Nguyen-Dumont, Tú et al., Abridged adapter primers increase the target scope of Hi-Plex, BioTechniques, 58, 33-36, 2015, US.
Nimagen, Low-plex Targeted Genotyping by NGS, NimaGen, N/A, 1-4, 2020.

(Continued)

*Primary Examiner* — Juliet C Switzer
*Assistant Examiner* — Brian Ellis Young
(74) *Attorney, Agent, or Firm* — JONES DAY

(57) ABSTRACT

A method of preparing a library of library constructs by multiplex amplification for use in targeted next generation sequencing is described. The method comprises the steps of: (a) providing a reaction vessel comprising (i) a plurality of different target sequences, (ii) a plurality of target capture primer pairs, and (iii) one or more tagging primer pairs, (b) performing sequential rounds of amplification at sequential annealing temperatures configured to amplify the target sequences, generate target sequences comprising first or second read sequences, and provide a reaction product comprising library constructs in a sequential manner; and (c) capture of the library of constructs from the reaction product. One of the forward and reverse tagging primers comprises a purification label at the 5' end, and is provided at a limiting concentration whereby the library constructs comprises an abundance of partial constructs containing only one indexing sequences and only one adapter sequences, and a limited number of full (complete) constructs containing the first and second indexing sequences, the first and second adapter sequences and the purification label. The capture step comprises capturing the full (complete) constructs from the reaction product using the purification label.

15 Claims, 4 Drawing Sheets

(56)　　　　　References Cited

OTHER PUBLICATIONS

Pope, Bernard J. et al., Hi-Plex for Simple, Accurate, and Cost-Effective Amplicon-based Targeted DNA Sequencing, Next Generation Sequencing: Methods and Protocols, Chapter 5, 53-70, 2018.
Chung et al., 2017, "Genotyping-by-sequencing: a promising tool for plant genetics research and breeding," Hortic. Environ. Biotechnol., 58:425-431.

* cited by examiner

MULTIPLEX METHOD OF PREPARING A SEQUENCING LIBRARY

CROSS-REFERENCE TO RELATED APPLICATIONS

This application is a national stage entry under 35 U.S.C. §371 of PCT/EP2020/075529 filed Sep. 11, 2020, which claims priority to EP application Ser. No. 19/198, 454.1 filed Sep. 19, 2019, which claims priority from and the benefit of U.S. Provisional Application No. 62/898,752 filed Sep. 11, 2019.

FIELD OF THE INVENTION

The present invention relates to a multiplex amplification method of preparing a library for use in targeted next generation sequencing. Also contemplated are methods of targeted next generation sequencing incorporating multiplex amplification.

BACKGROUND TO THE INVENTION

Targeted genotyping by sequencing (GBS) involves pooling indexed and adapter linked multiplex amplification products into a single library sample for a high-throughput next generation sequencing run. From this sequencing data individual genotype profiles are extracted and compiled through bioinformatic tools involving demultiplexing and allele counting. Several modifications of this principal method exist, both open source and commercial (Eureka and AgriSeq Thermofisher, Nugen Allegro, Keygene SNPselect, LGC SeqSNP, AgriPlex Genomics PlexSeq). The open source methods rely often on enzymatic amplification both in the enrichment and actual library preparation.

Developing an in-house workflow for targeted GBS methods can be divided into following processes as follows;
1. Target specific multiplex amplification
2. Sample indexing, sequencing primer and adapter addition
3. Normalisation & Size selection
4. QC & final library pooling
5. Next generation sequencing
6. Data analysis In all above-mentioned methods target amplification and library preparation are conducted in multiple steps (steps 1 to 4). The first reaction is a multiplex AMPLIFICATION of all targets in the panel. Having high number of targets in the same amplification reaction can cause issues through unspecific binding and formation of primer dimers. Hence, achieving efficiently working assay panel, the multiplex nature of the initial reaction needs to be taken into consideration at the primer design step to avoid problematic sequences. The final panel will be fine-tuned through testing iterations of the process in small scale. Multiplexing levels up to ~500 are commonly reported by the amplification-based methods (GT-Seq, MonsterPlex, Hi-plex, PlexSeq). The MonsterPlex (referenced in the literature to be like Hi-Plex) has an expectancy of around 85-90% of the markers to work when first run. These libraries are sequenced with high depth, ~500K reads per sample, to get good coverage. The Hi-Plex method, also amplification based, claims plexing levels up to 1000 (Nguyen-Dumont et al. 2013, Nguyen-Dumont et al. 2015, Pope et al. 2018, Hammet et al. 2019). Hi-Plex is the only method which aims to combine the two amplification steps; the indexing/adapter introducing primers are spiked into to the multiplexing reaction after initial amplification. Hence the method still requires opening and re-sealing of the sample plate. The key aspects listed by the authors in the principle process are high-fidelity Taq enzyme, permissive initial amplification conditions allowing for a range of targets to be amplified simultaneously, followed by bulk of amplification against tails added by target specific primers, and relatively long cycles allowing for complete priming and extension. The method initially published for a 60-plex panel, was further developed to achieve the 1003-plex by adding another set of so-called short bridge-primers to the multiplex. Here the target specific amplification mix has two shorter primers, complementary to part of the tails added by target specific primers. Bulk of amplification would be conducted in the first part using target specific and bridge primers. Indexing primers are not added to the mix until the last four cycles. This is different to their initial 60-plex method, not utilising short bridge primers, where the bulk of amplification took place after the indexing primers were added. Recent publication from Hammet et al. (2019) describes further updates on Hi-Plex method to improve on-target amplification. In the updated method the initial two step amplification using target specific and tagging primers has less cycles, followed by size selection prior proceeding to another amplification to amplify the constructed library, but still requires opening and re-sealing of the sample plate. The short generic bridge primes are not utilised anymore. Hammet's comparison between the previous and current method shows similar performance at lower plexing levels <300 but at higher target numbers the updated method has improved capacity.

Consistent annealing among target primers is paramount for more equal amplification of several targets concurrently. Rather than with longer cycles at a single temperature common to all Hi-plex versions, GT-Seq methods acknowledge this by including a slow ramp from 95° C. to 57° C. to allow more accurate annealing with 10 amplification cycles. Chen et al. (2016) describe another way to level the amplification by using limited primer availability; the multiplex amplification product is used as a target in a second amplification step without adding further primers. This reaction is let to run to use up all available primers prior proceeding to indexing and should yield to a more normalised output (authors referred the method as three-round amplification). Introducing third amplification reaction is not ideal but validating correct primer availability in the multiplex could be helpful. Like Hi-plex, GT-Seq and Monsterplex methods use premium Taq enzymes.

To enable pooling samples together into a single sequencing run, each sample requires unique labelling. This can be done by unique combinations of short sequences (e.g. 6- or 8-mers) in both ends or just one end of the DNA sample. To enable thousands or tens of thousands of individuals to be sequenced in the same indexing run, a systematic indexing approach is required; such as one index denoting the well position and the other denoting the plate. This high density sample pooling can be achieved by re-using 96- or 384-well specific indexes by combining them with different plate indexes. In the amplification based targeted GBS methods, indexing is enabled through target specific multiplex primers carrying a generic tail sequence; forward primers share the same tail sequence, distinct from the tail shared by the reverse primers. These tails are then targeted in the second amplification step, conducted by primers adding unique indexes and sequencing adapters. Further, the generic tails introduced by target specific primers, function as sequencing primer targets at the sequencing reaction. Following the second amplification step, sample specific libraries containing multiplexed targets are achieved.

The process linking these two reactions together can vary. Like already mentioned Chen et al. (2016), an amplification step can be included between these two to exhaust all the target specific primers. In GT-Seq the amplification product from the multiplexing reaction is diluted prior to acting as a target in the second index/adapter adding amplification on a new plate. The Hi-Plex method uses different approach; indexing primers are added directly to the initial amplification plate. There is no in-between dilution step. The reaction uses the enzyme mix added in the first amplification set up, approach which saves both reagents and plates. The plate still needs to be either pierced or peeled, and further resealed. The last step could prove difficult in high-throughput applications due to risk of contamination of samples, notably where water-bath based thermal cycling is employed.

GB2536446 describes a single, closed tube PCR method of generating amplicon constructs of a target sequence by means of reverse complement PCR (RC-PCR). The method employs (a) an oligonucleotide probe comprising a universal sequence and, at or towards its 5' end, a target specific sequence capable of hybridising to the reverse compliment of a sequence at, or flanking one of the 3' ends of the target sequence and (b) a universal primer comprising at its 3' end a sequence capable of hybridising to the universal sequence of the oligonucleotide probe. One key element of this process is that it does not incorporate a normalisation step, and instead employs a blocking group in the RC-PCR method at the initial step when creating the full length oligos for the target amplification+adapter addition, which prevents the target specific oligos not binding until full length oligos are made. While this may help with target evenness, the lack of normalisation in the method would cause some of the samples overpowering the others during sequencing and use up lot of the data. This severely limits the number of targets that this method can process accurately. Referring to the Nimagen website (https://www.nimagen.com/applications/greenotype), this method (GREENOTYPE RC-PCR) is marketed for genotyping no more than 100 targets, whereas a different method (GREENOTYPE MIP CAPTURE) is marketed for higher throughput (up to 5000 targets). Thus, the RC-PCR method as disclosed in GB2536446 is not suitable for processing high number of targets.

Meldgaard et al. (Clinica Chimica Acta, Vol. 413; No. 19 (2012) and WO2017/044100 (Insilixa Inc.) both describe methods of target amplification and library preparation that employ asymmetric PCR for producing single stranded products that are captured on a printed array or beads followed by analysis on a flow cytomer. Single stranded products are made when there is an excess of one of the 2 primers in each set and once the limiting primer is used up. The single stranded products are amplified linearly rather than exponentially. In both of these examples the end goal is to produce these single stranded products that can then be captured through hybridization. Neither method is suited to targeted high throughput (NGS) sequencing or sample pooling.

Bybee et al. (Genome Biology and Evolution, Vol. 3, 1 Jan. 2011) describes a method of generating a library of sequences by multiplex PCR method that employs a single inline barcode with Roche 454 sequencing, which limits the number of samples that can be run at once. The method requires a first PCR reaction in a first vessel prior to aliquoting of the first reaction product into a second vessel for the second PCR step. The two PCR step method is laborious and time consuming, and the need to transfer product between vessels introduces the risk of cross-contamination between samples. The method involves a step of bead immobilization as part of the emulsion PCR step required for Roche 454 sequencing. In this method, each individual sample is quantified using pico-green and then normalized using a liquid handling robot, which is time consuming and expensive.

It is an object of the invention to overcome at least one of the above-referenced problems.

SUMMARY OF THE INVENTION

The present invention provides a single, closed-tube method, of preparing a library construct for use in targeted high throughput sequencing by multiplex amplification, without the need for reopening the tube to add further ingredients. The present invention also has a build in normalisation so that a separate normalisation step is not necessary. Referring to FIG. 1, the method employs a target capture primer pair specific to each target in a sample, and a tagging primer pair specific to the sample. Each target capture primer pair comprises forward and reverse primers comprising a target specific sequence and a read sequence, where the target specific sequences are configured to bind to the template nucleic acid at positions flanking the target (step 1). The tagging primer pair includes forward and reverse tagging primers each having an adapter sequence (P5, P7), an indexing sequence (xxxxx), and a sequence that binds to the read sequences (read sequence primer site) (step 2). Initial amplification steps (FIG. 1(1)) generates an intermediate construct containing the target sequence flanked by read sequences (R1 and R2). In subsequent amplification steps (FIG. 1(2)), the tagging primers bind to the intermediate construct by the read sequence primer sequences annealing with the read sequences. In the method of the invention, one of the tagging primers is providing in limiting concentrations and also includes a purification tag (B), which results in a reaction product containing partial and complete constructs (FIG. 1(3)). The partial constructs comprise target sequence but only one adapter sequence (P5) and one index sequence (xxxxx). On the other hand, the complete construct contains target sequence, first and second adapter sequences (P5, P7) and first and second indexing sequences (xxxxx) and the purification tag. Due to the use of a limiting amount of one of the tagging primers (in the case illustrated, the reverse tagging primer), the reaction product contains an excess of partial constructs to the complete constructs, with the result that each individual reaction produces complete sequencing constructs with approximately the same amount of each targeted locus in relatively equal abundance over a wide range of template DNA (i.e. self-normalisation). It should be understood that in FIG. 1 the read sequences R1, R2, and the adapter sequences P5, P7, are for exemplification purposes only, and that any read sequence, indexing sequence and adapter sequence can be used, which are known to the skilled person.

With the method of the invention, target capture, indexing and adapter addition take place in the same reaction vessel without opening the reaction vessel, followed by library capture using the purification label. Following the amplification reaction samples can be pooled together from thousands of individual reactions with capture and purification of completed library constructs achieved using the purification label (biotin in the example of FIG. 1). The unique combination of first and second index sequences (e.g., i5 and i7 barcode sequences) in each reaction allows pooling of all samples following multiplex amplification without risk of cross contamination. When the number of the target specific primers can vary depending on desired assay panel, only two unique tagging primers are required per reaction. Initial amplification is conducted using target capture primers amplifying the desired genomic DNA sites. After first two rounds of amplification partial binding sites for tagging primers are created and they can start annealing to their complements. In the next few cycles full length complements for the tagging primers are created and once this has taken place, the rest of the reaction is conducted at a higher annealing temperature reflecting the complete priming sites for tagging primers. The method of the invention is applicable for multiplex amplification of multiple samples (e.g. up to 200,000) in which each sample comprises thousands of target sequences (e.g. SNP's), all of which can be performed in a single closed tube. For a sample with, for example, 50 target sequences, the method employs 50 target specific primer pairs, and one tagging primer pair (specific for the sample). When the method is applied to multiple samples, for example 500 samples, each having 50 target sequences, the method employs 50×500 target specific primer pairs, and 50 tagging primer pairs (one for the sample). Amplification may be performed by polymerase chain reaction (PCR) or by other enzymatic nucleic acid amplification techniques.

Compared with the method of Bybee et al, the method of the invention allows the target capture primer pairs and tagging primer pair(s) to be included in the same reaction vessel and incubated together at the same time from the beginning and during the amplification steps. This speeds up and simplifies the processing and reduces the risk of cross-contamination which is an inherent problem with 2-step PCR processes such as Bybee where reaction products of the first PCR step have to be cleaned before being aliquoted into a second reaction vessel for the second PCR step. In addition, the incorporation of a self-normalisation step in the method of the invention obviates the requirement for each sample to be individually quantified and then normalized using a liquid handling robot, which is time consuming and expensive.

Compared with the method of GB2536446, the incorporation of a self-normalising step in the method of the invention overcomes the problem of low throughput and allows multiplex amplification in a single vessel of hundreds or thousands of targets, from multiple samples, in a single run without compromising target evenness, irrespective of different samples having different concentrations or quality of target DNA.

In a first aspect, the invention provides a method of preparing library constructs by multiplex amplification for use in targeted high throughput sequencing, comprising the steps of:

(a) providing a first reaction vessel comprising:
    (i) at least one sample comprising a plurality of different target sequences;
    (ii) a plurality of target capture primer pairs for the at least one sample, in which each target capture primer pair comprises:
        a forward primer comprising in a 5' to 3' direction a first read sequence and a target specific sequence; and
        a reverse primer comprising in a 5' to 3' direction a second read sequence and a target specific sequence;
    (iii) a tagging primer pair for the at least one sample comprising:
        a forward tagging primer comprising in a 5' to 3' direction a first adapter sequence, a first indexing sequence, and a first read sequence primer site; and a reverse tagging primer comprising in a 5' to 3' direction a second adapter sequence, a second indexing sequence, and a second read sequence primer site,
(b) performing sequential rounds of amplification at sequential annealing temperatures configured to amplify the target sequences, generate target sequences comprising first and second read sequences, and provide a reaction product comprising adapter-ligated library constructs in a sequential manner; and
(c) capture of the adapter-ligated library constructs from the reaction product,
characterised in that one of the forward and reverse tagging primers comprises a purification label at the 5' end and is provided at a limiting concentration whereby the library of adapter-ligated constructs comprises:
    partial constructs containing only one of the first and second indexing sequences and only one of the first and second adapter sequences; and
    complete constructs containing the first and second indexing sequences, the first and second adapter sequences and the purification label,
wherein the reaction product comprises an excess of partial constructs to complete constructs, and wherein step (c) comprises capture of only the complete constructs comprising the purification label.

Typically, isolation (capture) of the complete library constructs from the reaction product comprises bringing the reaction product into contact with a support comprising a ligand for the purification label.

The sample consists of or comprises nucleic acid containing the target sequence(s). Generally, the sample is DNA. The target sequences are generally sequence variations, for example single nucleotide polymorphisms (SNP's) or short indels.

The capture step typically comprises reacting the reaction product with a support comprising a ligand for the purification label. The purification label may be biotin, and the support may comprise streptavidin (for example streptavidin beads). Other purification labels and capture ligands may be employed, the details of which will be known to a person in the art.

The complete library constructs may be released from the support, for subsequent high throughput sequencing, or it may be amplified in a multiplex amplification step while still attached to the support to provide an amplification product which may then be sequenced using high throughput sequencing. In one embodiment, a plurality of amplification cycles is performed and the amplification product is typically separated from the isolation support.

Generally, steps (a) and (b) are performed in a closed vessel (e.g. tube) typically without the vessel being opened until the steps have been performed.

The thermal cycling of the amplification steps is configured to amplify the target sequences, generate target sequences comprising first and second read sequences, and provide a reaction product comprising adapter-ligated library constructs in a sequential manner. In the embodiments described, using Illumina R1 and R2 read sequences, and i5 and i7 indexing sequences, the thermal cycling employs initial, intermediate and final rounds of amplification with increasing annealing temperatures. It will be appreciated that when read sequences and indexing sequences from different sources are employed, different thermal cycling protocols may be employed. The use of Illumina read and indexing sequences is exemplary and not intended to limit the scope of the application.

Thus, for example, the sequential rounds of amplification at sequential annealing temperatures may comprise:

(i) performing one or more initial rounds of amplification in the reaction vessel at a first annealing temperature;

(ii) performing one or more intermediate rounds of amplification in the reaction vessel at a second annealing temperature configured to generate target sequences comprising first and second read sequences; and (iii) performing one or more final rounds of amplification in the reaction vessel at a third annealing temperature configured to provide a reaction product comprising a library of library constructs including partial constructs and complete constructs.

Generally, the second annealing temperature is higher than the first annealing temperature, and the third annealing temperature is higher than the second annealing temperature. However, different sequential annealing temperatures may be employed depending on the context.

In one embodiment, the first annealing temperature is 62° C.+/−5° C., the second annealing temperature is 67° C.+/−5° C., and the third annealing temperature is 72° C.+/−5° C.

In one embodiment, the sequential rounds of amplification comprise 1-5 initial rounds of amplification (preferably 1-3 or 2 rounds), 1-5 intermediate rounds of amplification (preferably 2-4 or 3 rounds), and at least 10 final rounds of amplification (for example 10-50).

In one embodiment, the purification label is biotin, and the isolation step comprises reacting the reaction product with streptavidin beads.

In one embodiment, steps (a) and (b) are performed on a plurality of samples, wherein the reaction products for the different samples are pooled and the capture/isolation step (c) is performed on the pooled reaction products. In one embodiment, steps (a) and (b) are performed on 2 to 200,000 samples, for example at least 100, 1000, 10,000, 20,000, 50,000, 100,000, 150,000 or 200,000 samples and then pooled. In one embodiment, steps (a) and (b) are performed in a well of a microtitre plate. In one embodiment, each sample comprises 1-10,000 target sequences, for example at least 10, 50, 100, 500, 1,000, 2,000, 3,000, 4,000, 5,000, 6,000, 7,000, 8,000, 9,000 or 10,000 target sequences.

Amplification is generally performed by polymerase chain reaction (PCR). It will be appreciated that in order to perform PCR on a target sequence, additional reagents are required and that those reagents will depend on the type of PCR employed. For example, to perform PCR, the method of the invention employs a heat-stable DNA polymerase (e.g. Taq polymerase), and all four deoxyribonucleotides (dATP, dTTP, cCTP, cGTP).

In another aspect, the invention provides a method of targeted high throughput sequencing comprising the steps of:

providing a library of complete constructs according to a method of the invention; and performing high throughput sequencing on the library of complete constructs.

In a preferred embodiment, the high throughput sequencing is a next generation sequencing technique. One example is illumina dye sequencing, in which the adapter sequences (and typically the target primer pairs and tagging primer pairs) are configured for use with illumina dye sequencing.

In one embodiment, the high-throughput sequencing has an on-target rate of at least 30%, 40%, 50% or 60%.

The methods of the invention may be employed to genotype a sample, for medical, diagnostic or commercial purposes. In one embodiment, the methods of the invention may be employed to confirm, genetically, the source or identity of a food product, for example a meat, fish, game, vegetable, pulse, grain, or fruit product.

In another aspect, the invention provides a kit for preparing library constructs by multiplex amplification suitable for use in targeted high throughput sequencing of one or more samples, the kit comprising a tagging primer pair for each sample, each tagging primer pair comprising:

a forward tagging primer comprising in a 5' to 3' direction a first adapter sequence, a first indexing sequence, and a first read sequence primer site; and a reverse tagging primer comprising in a 5' to 3' direction a second adapter sequence, a second indexing sequence, and a second read sequence primer site wherein only one of the forward or reverse tagging primer comprises a purification label at the 5'-end.

In one embodiment, the kit comprises a plurality of target specific primer pairs (one per target sequence per sample), in which each primer pair comprises:

a forward primer comprising in a 5' to 3' direction a first read primer sequencing site and a target specific sequence; and a reverse primer comprising in a 5' to 3' direction a second read primer sequencing site and a target specific sequence;

In one embodiment, the purification label is biotin.

In one embodiment, the kit comprises a support comprising streptavidin, for example beads or magnetic beads coated with streptavidin.

In one embodiment, the target primer pairs and tagging primer pairs are configured for use with illumina dye sequencing.

Other aspects and preferred embodiments of the invention are defined and described in the other claims set out below.

Phase 1: Initial amplification set up containing template DNA with the target SNP site identified with the star. The forward and reverse target capture primers are illustrated annealing to the template DNA at positions flanking the target sequence via their respective Illumina target specific sequences. The tagging primers are also illustrated:

Forward tagging primer comprises in a 5' to 3' direction first adapter sequence, first indexing sequence, and read sequence primer site; and Reverse tagging primer comprises in a 5' to 3' direction a biotin purification tag (B), adapter sequence, indexing sequence, and read sequence primer site Phase 2: Partially formed DNA constructs following the initial low annealing temperature amplification cycles along with incorporated read sequences R1 and R2.

Phase 3: In the final phase amplification is allowed to proceed for many cycles creating an abundance of partial constructs (containing target sequence, R1 and R2 read sequences, one adapter sequence (P5) and one indexing sequence), while producing a set amount of complete library constructs (containing target sequence, R1 and R2 read sequences, two adapter sequence (P5 and P7) and two indexing sequence), due to the limited biotin labelled reverse tagging primer.

Figure 2:
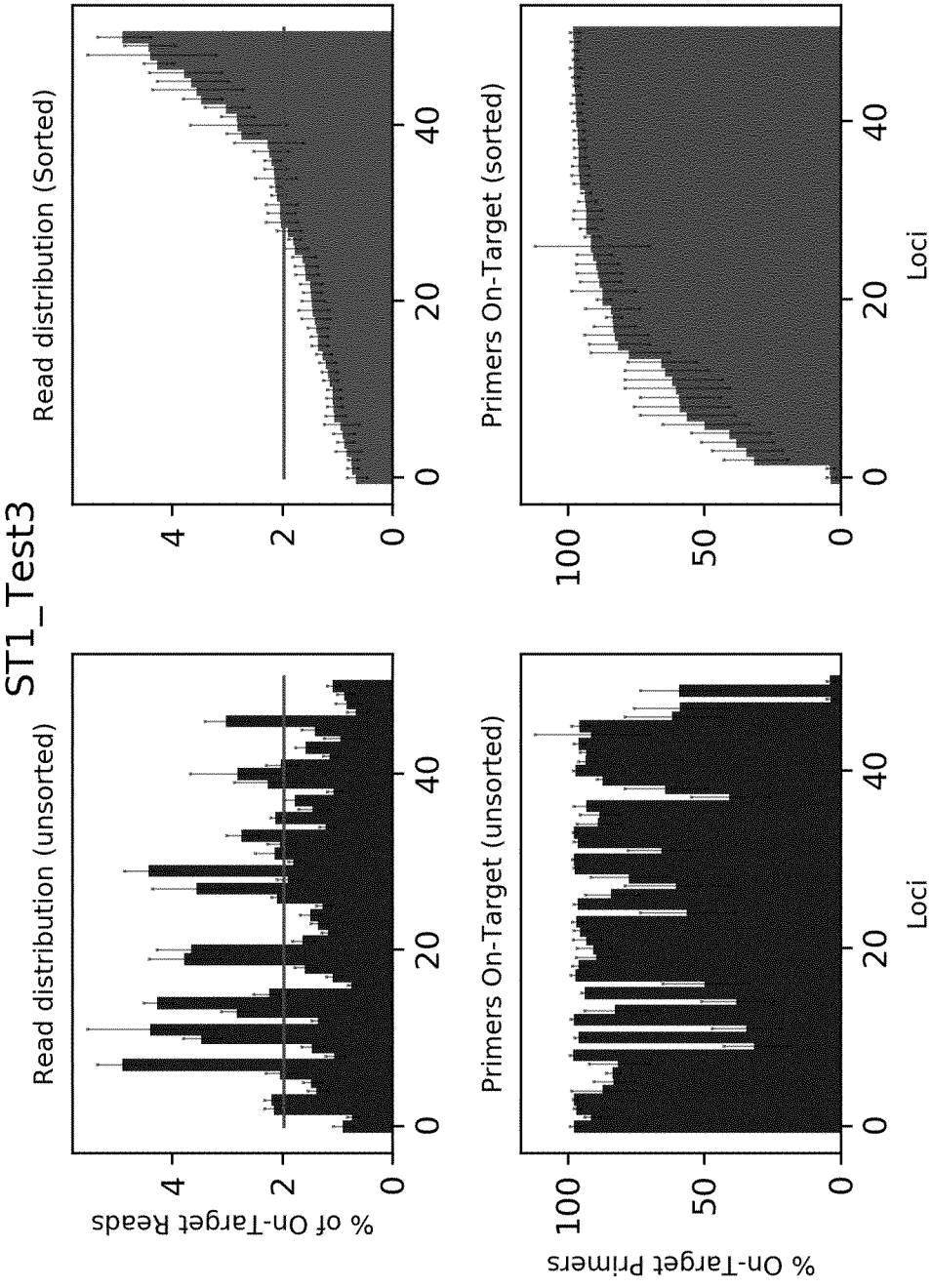

FIG. 2. Read distribution among loci and percentage of forward primers also containing target sequence.

9

Figure 3:
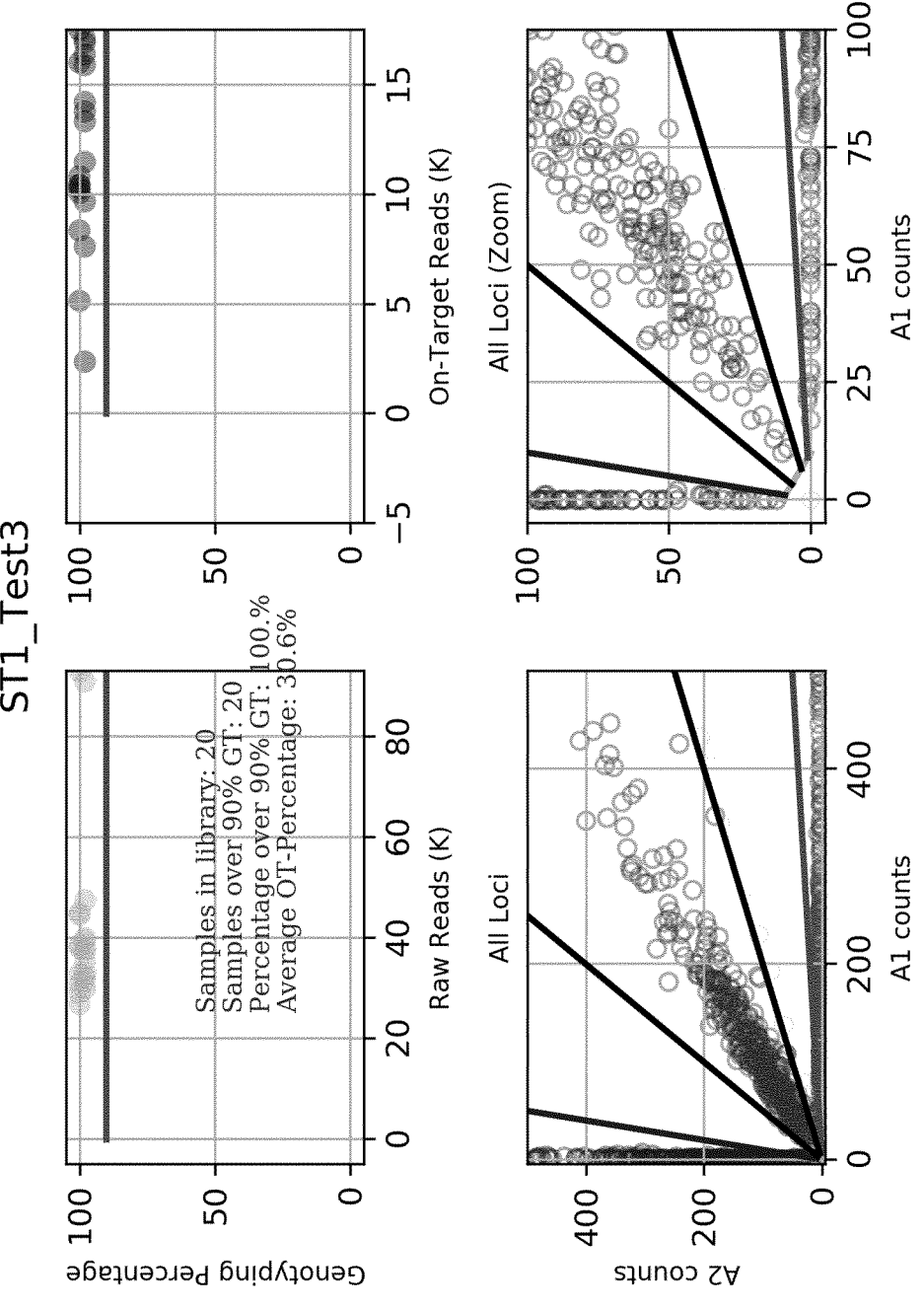

FIG. 3. Read distribution among samples and summary data.

Figure 4:
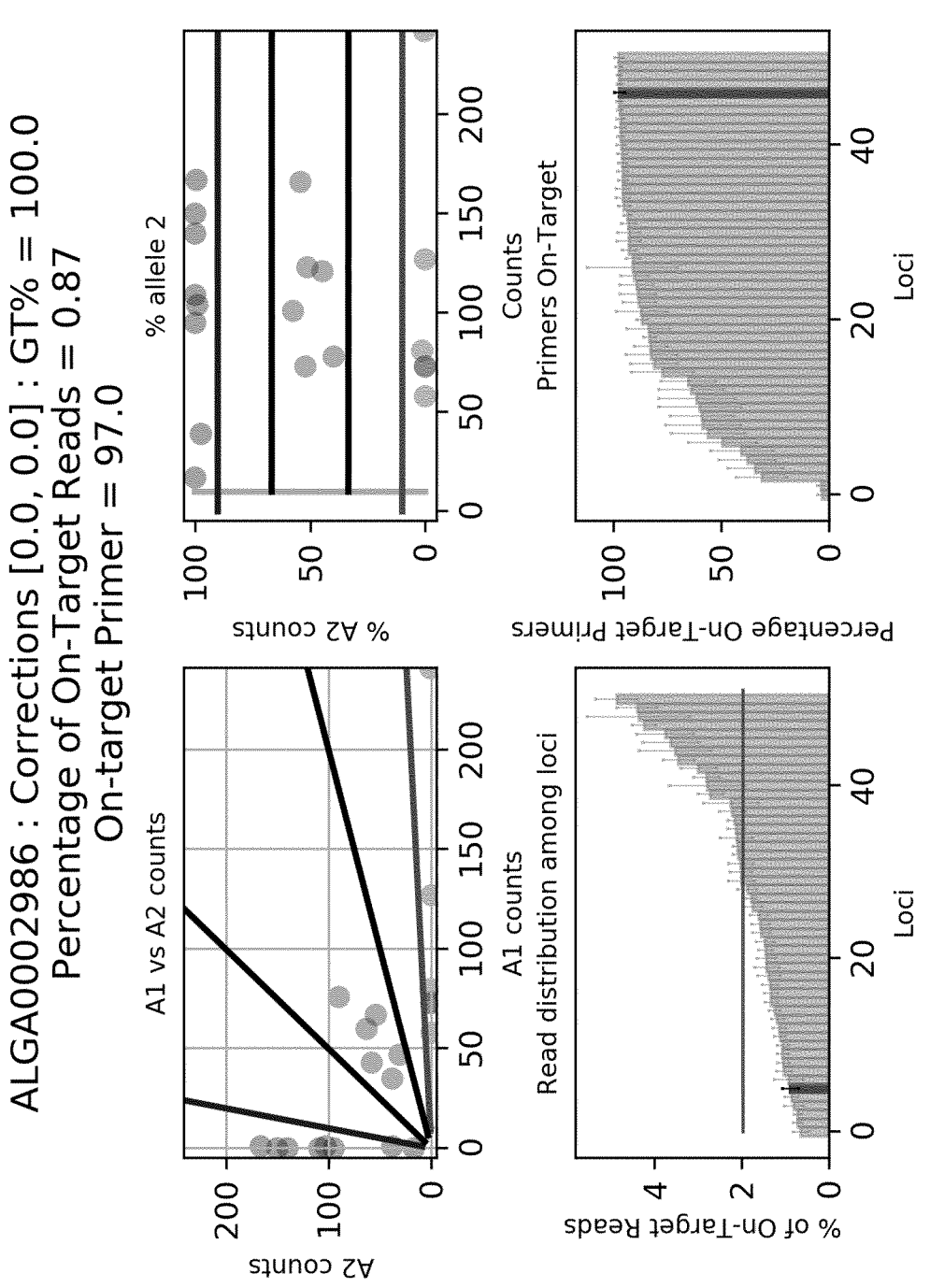

FIG. 4. Example of a single locus scatter plot. Each data point is a single sample.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

"Target sequence" refers to a sequence to be amplified, for example a variation in a nucleic acid sequence such as a polymorphism (for example a single nucleotide polymorphism (SNP) or a short indel). The nucleic acid sequence may be any part of genomic nucleic acid, for example a coding or non-coding part of a genome.

"Sample" refers to a composition comprising nucleic acid that contains the target sequence(s). The sample will generally be nucleic acid (e.g. DNA) that has been purified from a sample of biological material (e.g. tissue). Other nucleic acids that may be amplified include cDNA. The DNA to be amplified may be obtained from any part of the genome of any organism. For example, the DNA may be obtained from the human or other animal genomes, plant genome, fungal genome, bacterial genome, viral genome or any other DNA molecule. Methods of separating nucleic acid from biological matter and tissue samples are well known to a person skilled in the art. The method of the invention may be performed on a single sample containing multiple targets, multiple samples containing single targets, or multiple samples each containing multiple targets. The method of the invention is particularly applicable to use with multiple targets, for example greater than 100, 200, 300, 400 or 500 targets from one or more samples.

"High throughput sequencing" refers to sequencing in which a number of different target sequences are sequenced in parallel in the same reaction. The term includes "next generation sequencing" or "NGS" (also referred to as "deep sequencing" or "massively parallel sequencing") which is a DNA sequencing technology that performs sequencing of millions of small fragments of DNA in parallel. Various NGS techniques exist, including Sequencing by synthesis (Illumina), Pyrosequencing (454), Ion semiconductor (Ion Torrent Sequencing) and Combinatorial probe anchor synthesis (cPAS-BGI-MGI). Targeted NGS is a next generation sequencing technique that focusses on amplicons and specific genes, and that employs amplification of the needed gene or amplicon by enzymatic amplification, which is then sequenced on a NGS platform. It is described in Bybee et al ("Targeted Amplicon Sequencing (TAS): A Scalable Next-Gen Approach to Multilocus, Multitaxa Phylogenetics". Genome Biology and Evolution. 3: 1312-1323. doi:10.1093/gbe/evr106. PMC 3236605) and Masser et al ("Targeted DNA Methylation Analysis by Next-generation Sequencing". Journal of Visualized Experiments. 96: 52488. doi: 10.3791/52488. PMC 4354667).

Figure 1:
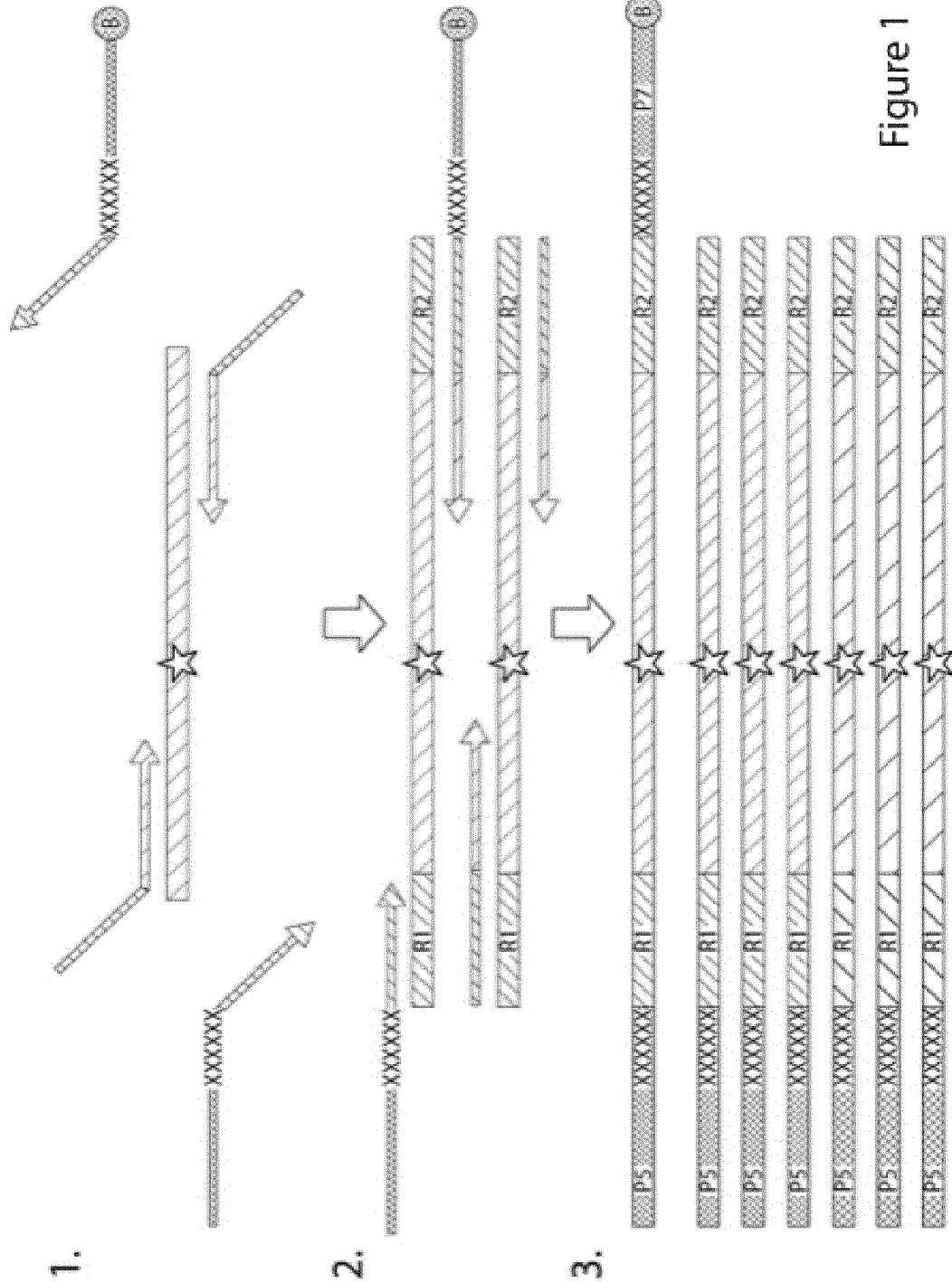
FIG. 1. Closed tube multiplex library construction.

"Library constructs" refers to a product of the multiplex amplification reaction of the invention that contains a target sequence and first and second adapter sequences to allow the construct be sequenced by a next generation or high throughput sequencing (NGS) technique. The construct generally also includes first and second read sequences that flank the target sequence (for example, the Illumina R1 and R2 sequences), and two indexing sequences that are disposed between the read sequences and the adapter sequences (for example, the Illumina i5 and i7 sequences). The library generally contains partial constructs, which contain only one adapter sequence and no purification label, and full (or complete) constructs which contains both adapter sequences required for NGS, both index sequences, and the purification label. A capture technique employing the purification label allows the complete construct to be captured and employed in NGS. Full (complete) and partial adapter library constructs are shown in FIG. 1 (phase 3).

"Adapter sequence" is a sequence of DNA configured to allow the adapter-ligated library constructs be sequenced by a next generation sequencing technique, for example any of the NGS techniques described herein including Illumina dye sequencing in a flow cell. The adapter sequences may be configured to allow the adapter ligated constructs be sequences by any NGS techniques. Illumina's adapters are described in https://support.illumina.com/downloads/illumina-adapter-sequences-document-1000000002694.html. Adapter sequences for all major NGS platforms are supplied by IDT (Integrated DNA Technologies) of Coralville, Ohio, USA (xGen™ UDI-UMI Adapters, xGen™ Stubby Adapters). IDT also provides a Custom Adapter Configurator tool that provides guidance on the design of Custom NGS Adapters.

"Read sequence" is a section of the target specific primer. Both primers in a target specific primer pair will include a read sequence. The read sequence is incorporated in the amplification product when the target DNA is amplified and forms a sequence to which the tagging primer can anneal via the tagging primer read sequence primer site. Examples of read sequences may include the Illumina R1 and R2 read sequences. Read sequences may also be obtained from Thermo Fisher as part of their Ion AmpliSeq™ DNA panels and library kits (https://www.thermofisher.com/ie/en/home/life-science/sequencing/next-generation -sequencing/ion-torrent-next-generation-sequencing-products-services/sequencing -reagents.html). "Read sequence primer site" is a section of the tagging primer that is complimentary to one of the read sequences and allows the tagging primers to anneal with target DNA that contains one of the read sequences.

"Indexing sequence" is a section of the tagging primer that is incorporated into the final library construct and that acts as a barcode to identify the construct when analysing the sequencing data. Generally, the indexing sequence is 6-8 nucleotides in length, and is positioned in the tagging primer between the read sequence primer site and the adapter sequence. A tagging primer pair will include two different indexing sequences, both of which will be incorporated into the full (complete) library construct. An example of indexing sequences are the Illumina i5 and i7 indexing sequences and the indexing oligonucleotides described in US2018334712. Suitable indexing sequences can be created using commercial products, for example:

https://rdrr.io/bioc/DNABarcodes/
https://omictools.com/dnabarcodes-tool

In the method of the invention, the tagging primer comprising the purification label is provided at "limiting concentration". This means that it is provided a concentration that results in there being insufficient tagging primer to bind to the partially formed DNA constructs, resulting a final product in which the partial constructs (with no purification label) is in excess, and in which the full (complete) construct containing the purification label is limited. This together with uniform initial target amplification, enables equal output across the samples obviating the need for sample specific downstream normalisation. In the example provided in FIG. 1, the reverse tagging primer containing the P7 adapter sequence is provided at a limiting concentration.

"Purification label" refers to a label that can be incorporated at an end of a primer sequence, and that can be used to purify a product of multiplex amplification. Typically, the label is an affinity label, configured for purification of amplification products using a support containing a ligand for the affinity label (for example streptavidin beads). In one embodiment, the label is biotin, the details of which will be known to a person skilled in the art. Other purification labels that may be employed in the methods and products of the present invention include oligonucleotide tags (Acridite).

"On-target rate" refers to the % of returned sequence data that are specific to the target region(s). The higher the on-target rate the more efficient is the use of the sequence run.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

The present invention provides a method for a single tube preparation of targeted library for next generation sequencing incorporating a normalization step using purification labels such as biotin labels. Typically, multiplexed library preparation has two steps; target capture followed by tagging and adapter addition. In many methods of the prior art both steps are generally achieved via amplification. Generally the two amplification steps are performed separately with purification steps. Hi-plex is a method which aims to combine these two amplification steps, however also in Hi-plex the indexing/adapter introducing primers are spiked into to the multiplex reaction after initial amplification. This means that the method still requires opening and re-sealing of the sample vessel. This is non-ideal for high-throughput processes (Nguyen-Dumont et al. 2013, Nguyen-Dumont et al. 2015, Pope et al. 2018, Hammet et al. 2019). The present invention relates to a truly single, closed-tube method, where target capture, indexing and adapter addition take place in the same reaction vessel followed by library capture using purification labels without the need to opening and resealing the sample vessels and without the need of purification steps before the tagging and adapter addition.

The idea of this method of the invention is that each individual reaction will produce complete sequencing constructs with approximately the same amount of each targeted locus in relatively equal abundance over a wide range of template DNA input. The unique combination of index barcode sequences in each reaction allows pooling of all samples following multiplex amplification without risk of cross contamination. Using a low concentration of the purification tag labelled tagging primer allows the multiplex amplification to produce an excess number of constructs containing only one adapter and indexing sequence while limiting the amount of completed library constructs. This together with uniform initial target amplification, enables equal output across the samples obviating the need for sample specific downstream normalisation and allows multiplex amplification of large numbers of targets from several hundred to several thousand. Following the amplification reaction samples can be pooled together from thousands of individual reactions with capture and purification of completed library constructs facilitated by the purification label, for example by using biotin as the purification label and streptavidin beads to capture to complete constructs bearing the biotin label. Overview of the single tube approach is shown in FIG. 1. Unlike in other methods, the target capture and tagging primers are all included in the same reaction vessel with their sequential activity guided by thermal cycling. When the number of the target specific primers can vary depending on desired panel, only two tagging primers are required per reaction. Initial amplification is conducted using target capture primers amplifying the desired genomic DNA sites. After first two rounds of amplification partial binding sites for tagging primers from the read sequence are created and they can start annealing to their complements. In the next few cycles full length complements for the tagging primers are created and once this has taken place, the rest of the reaction is conducted at a higher annealing temperature reflecting the complete priming sites for tagging primers.

The current indicative cycling conditions are shown in Table 1.

TABLE 1

| | Cycling conditions | | | |
|---|---|---|---|---|
| Step | Temp (° C.) | Time (s) | | Number of cycles |
| Initial hot start activation | 95 | 900 | | 1 |
| Target capture | 95 | 30 | | 5 |
| | 61 | 30 | −0.2° C./s | |
| | 72 | 30 | | |
| Tagging site formation | 95 | 30 | | 3 |
| | 67 | 30 | | |
| Tagging | 95 | 30 | | 22 |
| | 72 | 30 | | |

Primer Design

Target capture primers are designed such that the target specific 3' end had an annealing temperature (Tm) between 59° C. and 61° C. The primers are designed using a pipeline created for multiplex amplification to avoid most sources of downstream primer heterodimer artefacts. Target capture primers carry full length read sequence such as the Illumina R1 or R2 read sequences, matching the 3' end of the tagging primers. Each tagging primer contain a 6 base index barcode sequence sandwiched between the adapter sequence, such as the Illumina p5 or p7 capture sequence, and the read sequence primer site. This allows the use of dual index sequencing, such as that from Illumina, and allows demultiplexing of sequences from genetic data, such as fastq data, enabling downstream genotyping of individual samples. For example the p5 end of the constructs, the tagging primers may consist of the p5 sequence, a unique 6 base barcode sequence, and an Illumina read 1 sequencing primer site. While for the p7 end of the constructs the tagging primers consist of a biotin labelled 5' end, the p7 sequence, a unique 6 base barcode sequence, and an Illumina read 2 sequencing primer site. The overlapping sections of the primers typically have an annealing temperature of about 60° C. Once the full-length complement has been created, the Tm of the complete primer site is about 74° C. for each end of the construct.

Normalisation

The method does not require separate normalisation step after library construction. Rather the equal presentation of different samples is controlled by the cycling conditions and limiting the concentration of purification labelled tagging primers. Exhausting the tagging primer in the latter stages of thermal cycling, enables equal quantities of library complete constructs being bound on a support via the added purification tags; the total amount of construct between samples may vary but the fraction containing complete tag should be similar. Therefore, all samples can be pooled together after library construction and all downstream steps are conducted on single sample; library capture using purification support, library release from the support e.g. with short thermal cycling, final library clean-up e.g. using magnetic beads and library quantification. Suitable tagging primers are the i7 tagging primer from Illumina. Suitable purification tags are the biotin tags that can be capture with streptavidin beads.

Material

DNA used in the experiments was extracted from porcine ear tag tissue samples utilizing magnetic beads giving an average yield of 24 ng/μl (SD 11 ng/μl). All target capture primers were ordered from IDT at a synthesis scale of 25 nmoles at a concentration of 200 uM in Tris-EDTA pH 8.0 buffer using standard desalting purification. The biotin labelled i7 tagging primers were ordered lyophilized in tube format and resuspended in nuclease free water to a stock concentration of 10 uM.

Multiplex Amplification

Target capture primers were pooled and diluted to a concentration of 0.5 uM per each primer as a working stock. For the test library, a primer pool was created using 51 target capture primers. Individual reactions were set up as 7 uL total volume [3.5 uL Qiagen plus multiplex master mix, 2 uL DNA extract, 0.5 uL target capture primer mix, 1 uL 10 uM i5 tagging primer, ~0.01 uL biotinylated i7 tagging primer]. The amount of i5 tagging primer will need to vary depending on the number of target capture primers present in the pool so the molar amount of available primer sites is roughly equal to that of the i5 primer. In this case, the final concentration of all i5 tagging primer sites was ~1.8 uM and the concentration of the added i5 tagging primer used was ~1.4 uM in the final reaction conditions. The amplification was set up in a 96-well plate by first making a master mix by combining 52 uL pooled target primer mix, 1 uL 10 uM biotinylated i7 tagging primer, and 371 uL of Qiagen plus multiplex master mix (Qiagen, UK). To each well, 4 uL of master mix was dispensed followed by 1 uL of 10 uM i5 tagging primer, and 2 uL of template DNA using a multichannel pipette. Plate was heat sealed, vortexed gently, and briefly centrifuged. amplification was performed with following cycling conditions [95° C.—15 m (1×hot start); 95° C.—30 s, 61° C.—30 s (slow ramp 0.2° C./sec), 72° C.—30 s (5×); 95° C.—30 s, 67° C.—30 s (×3); 95° C.—30 s, 72° C.—30 s (×22); 4° C.—hold]].

Library Capture and Normalization

Following amplification, 4 uL of each reaction was combined into a single pool using a multichannel pipette. A 500 uL aliquot was combined with 500 uL of 2×binding buffer [10 mM Tris-Hcl (pH 7.5), 1 mM EDTA, 200 mM NaCl, and 0.02% Tween 20 buffer]. One microliter of streptavidin beads was washed in 1 mL of 1×binding buffer in a 1.5 mL tube and captured using a magnetic rack. The supernatant was discarded, the tube removed from the magnetic stand, and the magnetic beads were resuspended using 1 mL of the pooled amplification mixture. Beads were incubated at room temperature for 15 minutes and placed back on magnetic stand for approximately 3 minutes until the supernatant was cleared. While on magnetic stand the supernatant was removed and the beads were washed once using 1 mL of 1×binding buffer. Again, the supernatant was discarded, and the beads were resuspended in 20 uL of elution buffer (10 mM Tris-HCl pH 8.0). To release the captured library constructs from the beads another amplification is performed using the resuspended streptavidin beads. This single tube reaction was set up by mixing 20 uL Qiagen plus master mix (any PCR master mix could be used), 4 uL of 10 uM Illumina P5 primer, 4 uL of 10 uM Illumina P7 primer, and 12 uL of resuspended streptavidin beads. The amplification was performed using the following thermal cycling conditions [94° C.—15 m (hot start); 94° C.—30 s, 60° C.—30 s, 72° C.—30 s (5×); 4° C.—hold]. Following the 5 amplification cycles, the mixture was transferred to a fresh 1.5 mL tube and placed on the magnetic rack. A 25 uL aliquot of the cleared supernatant was transferred to a fresh 1.5 mL tube and mixed with 15 uL CleanNGS (CleanNA, Netherlands) beads. This mixture was incubated at room temperature for 5 minutes and the tube was placed back on the magnetic rack for 3 minutes. The cleared supernatant was then transferred to a fresh 1.5 mL tube and mixed with another 13 uL of CleanNGS beads. The mixture was again incubated for 5 minutes at room temperature and then placed on the magnetic rack for 3 minutes. The supernatant was removed and discarded and while still on the magnetic rack the beads were washed 2× using 200 uL of fresh 70% ethanol. The ethanol was removed, and tube was air-dried for 10 minutes to allow evaporation of residual ethanol. The bead pellet was then resuspended in 15 uL of elution buffer and the beads were captured on magnetic stand. The cleared supernatant was collected and transferred to a fresh 1.5 mL tube and 1.5 uL of elution buffer with 1% Tween 20 was added. This was the finalised library.

Library Quantitation

The concentration of the finalized library was determined using the Illumina library quantification kit from Kapa Biosystems (Roche Sequencing, US) per manufacturer's instructions on Applied Biosystems StepOnePlus instrument (Thermo Fisher Scientific, UK).

Sequencing and Data Analysis

The completed library was sequenced with an Illumina MiSeq instrument using a paired end 75 cycle kit. Following sequencing data was converted to fastq format using an Illumina conversion script that allows for the inclusion of the i7 and i5 index sequences to be added to the header line of each sequence. Sequencing reads were split into separate fastq files for each individual sample using the expected barcode combinations provided as an input file for the GTseq_BarcodeSplit_MP.py python script. Each individual fastq file was then used for genotyping using the GTseq_Genotyper_v3.pl perl script. Summary files containing genotypes, allele ratios, and other sequence read data were then analysed to assess the efficiency of the multiplex amplification library preparation method.

Results

The best performing conditions were tested on a set of 24 samples. Four samples were removed from analysis as these either contained no template, the reagents evaporated during PCR, or performed poorly under all tested conditions. For this subset of samples representing the presented conditions 835,017 raw reads containing expected 6-base barcode combinations were returned following sequencing. Evidence of evaporated wells due to poor heat sealing was noted prior to sequencing and as expected these wells returned poor numbers of reads. These samples were removed from further analysis as they didn't represent typical reaction conditions. Raw reads from each of the remaining individual samples (n=20) were relatively even with an average of 41,751 reads and a standard deviation of 18,068. The number of raw reads returned ranged from 26,890 to 93,038. The percentage of targeted sequences (as opposed to non-target or artifact sequences—also referred to as "on-target rate") averaged 31% among the 20 analysed samples. Even with low numbers of targeted reads there were enough reads for all 20 analyzed samples to genotype well and the average call rate was 98.9% with all having call rates above 98%. The evenness of reads among loci meant that not many reads were required to reach high call rates and the 90% threshold was met with as few as 2,400 on-target reads (FIG. 3). The selected target loci behaved as expected and produced clean allele ratios that were easily scored using the genotyping pipeline (FIG. 4).

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto. For brevity, embodiments are described as single embodiments, however it is to be understood that various combination of these embodiments are within the scope of the present invention.

REFERENCES

Hammet, F., Mahmood, K., Green, T. R., Nguyen-Dumont, T., Southey, M. C., Buchanan, D. D., Lonie, A., Nathanson, K., L., Couch, F. J., Pope, B. J. and Park, D. J. 2019: Hi-Plex2: a simple and robust approach to targeted sequencing-based genetic screening. BioTechniques. 67(3): 00-00 (September 2019). 10.2144/btn-2019-0026.

Nguyen-Dumont, Tu, Pope, B., Hammet, F., Southey, M. and Park, D. 2013: A high-plex PCR approach for massively parallel sequencing. Biotechniques. 55:69-74.

Nguyen-Dumont, T., Hammet, F., Mahmoodi, M., Pope, B., Giles, G., Hopper, J., Southey, M., and Park, D. 2015: Abridged adapter primers increase the target scope of Hi-Plex. BioTechniques. 58: 33-36.

Pope, B., Hammet, F., Nguyen-Dumont, T. and Park, D. 2018: Hi-Plex for simple, accurate, and cost-effective amplicon-based targeted DNA sequencing. Chapter 5 in Steven R. Head et al. (eds), Next Generation Sequencing: Methods and Protocols. vol. 1712.

16

The invention claimed is:

1. A method of preparing library constructs by multiplex amplification for use in targeted next generation sequencing, comprising the steps of:
   (a) providing a first reaction vessel comprising:
      (i) at least one sample comprising a plurality of different target sequences;
      (ii) a plurality of target specific primer pairs for the at least one sample, in which each primer pair comprises:
         a forward primer comprising in a 5' to 3' direction a first read sequence and a target specific sequence; and
      a reverse primer comprising in a 5' to 3' direction a second read sequence and a target specific sequence;
      (iii) a tagging primer pair for the at least one sample comprising:
         a forward tagging primer comprising in a 5' to 3' direction a first adapter sequence, a first indexing sequence, and a first read sequence primer site; and
      a reverse tagging primer comprising in a 5' to 3' direction a second adapter sequence, a second indexing sequence, and a second read sequence primer site,
   (b) performing in the first reaction vessel sequential rounds of amplification at sequential annealing temperatures configured to amplify the target sequences, generate target sequences comprising first and second read sequences, and provide a reaction product comprising a library of adapter-ligated constructs in a sequential manner; and
   (c) capture of the library of adapter-ligated constructs from the reaction product, characterised in that one of the forward and reverse tagging primers comprises a purification label at the 5' end and is provided at a limiting concentration whereby the library of adapter-ligated constructs comprises:
   partial constructs containing only one of the first and second indexing sequences and only one of the first and second adapter sequences; and
   complete constructs containing the first and second indexing sequences, the first and second adapter sequences and the purification label, wherein the reaction product comprises an excess of partial constructs to complete constructs, and wherein step (c) comprises capture of only the complete constructs comprising the purification label.

2. A method according to claim 1 in which the first reaction vessel is closed during step (b).

3. A method according to claim 1, in which the sequential rounds of amplification at sequential annealing temperatures comprise:
   (i) performing one or more initial rounds of amplification in the reaction vessel at a first annealing temperature;
   (ii) performing one or more intermediate rounds of amplification in the reaction vessel at a second annealing temperature configured to generate target sequences comprising first or second read sequences; and
   (iii) performing one or more final rounds of amplification in the reaction vessel at a third annealing temperature configured to provide a reaction product comprising a uniform amount of complete library constructs.

4. A method according to claim 3, in which the second annealing temperature is higher than the first annealing temperature, and the third annealing temperature is higher than the second annealing temperature.

5. A method according to claim 4, in which the first annealing temperature is 61° C. +/−5° C., the second annealing temperature is 67° C. +/−5° C., and the third annealing temperature is 72° C. +/−5° C.

6. A method according to claim 3, comprising 1-5 initial rounds of amplification, 1-5 intermediate rounds of amplification, and 10-20 final rounds of amplification.

7. A method according to claim 1, in which the purification label is biotin, and the capture step comprises reacting the reaction product with streptavidin beads.

8. A method according to claim 1, in which steps (a) and (b) are performed on a first sample in the first reaction vessel to generate a first reaction product comprising a first library of adapter-ligated constructs, and steps (a) and (b) are performed on a second sample in a second reaction vessel to generate a second reaction product comprising a second library of adapter-ligated constructs, wherein the first and second reaction products are pooled and the capture step (c) is performed on the pooled reaction products.

9. A method according to claim 8, in which steps (a) and (b) are performed on each of more than 100 samples.

10. A method according to claim 8, in which steps (a) and (b) are performed on each of at least 1000 samples.

11. A method according to claim 1, in which each sample comprises at least 10 target sequences.

12. A method according to claim 1, in which each sample comprises at least 50 target sequences.

13. A method according to claim 1, wherein the capture step comprises capture of the complete constructs on a support, and subsequent amplification of the complete constructs while attached to the support.

14. A method of targeted next generation sequencing comprising the steps of:

providing a library of complete constructs, wherein the library of complete constructs is prepared by the method of claim 1; and performing high throughput sequencing on the library of complete constructs.

15. A method according to claim 14, in which the next generation sequencing is illumina dye sequencing.

* * * * *